United States Patent [19]

Preis et al.

[11] Patent Number: 5,650,168
[45] Date of Patent: Jul. 22, 1997

[54] TABLET WITH IMPROVED BIOAVAILABILITY CONTAINING DICHLOROMETHYLENEDIPHOSPHONIC ACID AS THE ACTIVE SUBSTANCE

[75] Inventors: Walter Preis, Neustadt; Bernd Müsel, Worms; Günther Neugebauer, Mannheim; Rolf-Dieter Gabel, Schwetzingen, all of Germany

[73] Assignee: Boehringer Mannheim GmbH, Mannheim, Germany

[21] Appl. No.: 537,853

[22] PCT Filed: Jul. 24, 1993

[86] PCT No.: PCT/EP93/01967

§ 371 Date: Nov. 15, 1995

§ 102(e) Date: Nov. 15, 1995

[87] PCT Pub. No.: WO94/26310

PCT Pub. Date: Nov. 24, 1994

[30] Foreign Application Priority Data

May 15, 1993 [DE] Germany .................. 9307393 U
Jul. 2, 1993 [DE] Germany .................. 43 22 057.6

[51] Int. Cl.⁶ .................. A61K 47/38; A61K 9/20; A61K 31/66
[52] U.S. Cl. .................. 424/465; 424/468; 424/480; 424/482; 424/470; 424/474; 514/960
[58] Field of Search .................. 424/470, 468, 424/482, 465, 474; 428/480; 514/960

[56] References Cited

U.S. PATENT DOCUMENTS

| | | | |
|---|---|---|---|
| 4,840,799 | 6/1989 | Appelgren et al. | 424/493 |
| 4,859,472 | 8/1989 | Demmer et al. | 424/489 |
| 4,980,171 | 12/1990 | Fels et al. | 424/473 |

OTHER PUBLICATIONS

Chemical Abstracts 1975:175208, "Dissolution Rate and Bioavailability of Griseofulvin from A Ground Mixture With Microcrystalline Cellulose" 1975.

*Primary Examiner*—Frederick Krass
*Attorney, Agent, or Firm*—Nikaido Marmelstein Murray & Oram LLP

[57] ABSTRACT

The invention concerns tablets with improved bioavailability of the active substance dichloromethylenediphosphonic acid or of a physiologically tolerated salt thereof and with a content of microcrystalline cellulose as a pharmaceutical auxiliary substance, pharmaceutical packs containing these tablets, the use of the active substance dichloromethylenediphosphonic acid together with microcrystalline cellulose for the production of a tablet with improved bioavailability and the process for producing the tablet.

32 Claims, 1 Drawing Sheet

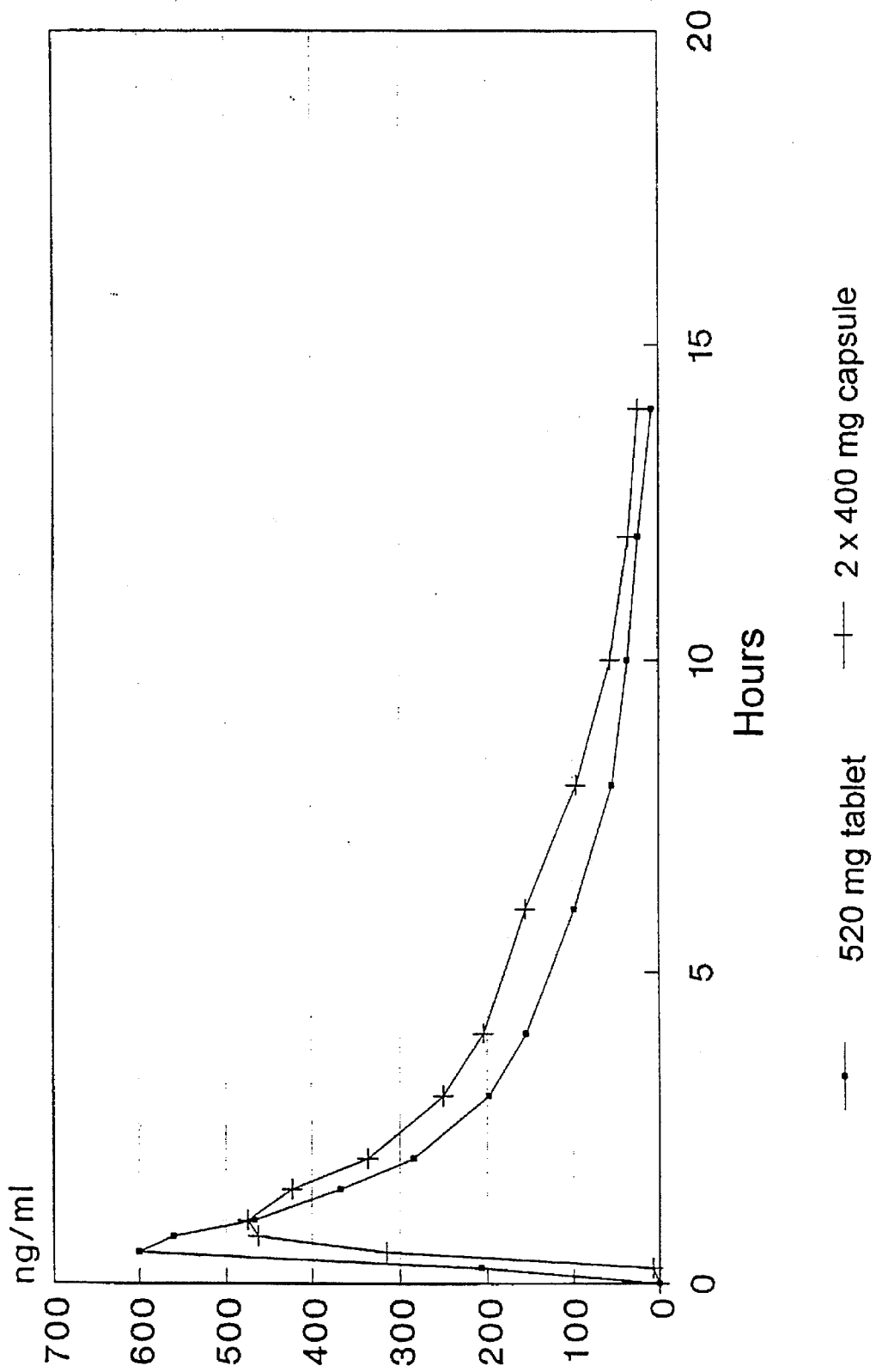

TABLET WITH IMPROVED BIOAVAILABILITY CONTAINING DICHLOROMETHYLENEDIPHOSPHONIC ACID AS THE ACTIVE SUBSTANCE

The invention concerns tablets with improved bioavailability of the active substance dichloromethylenediphosphonic acid (clodronic acid) or of a physiologically tolerated salt thereof and an additive of microcrystalline cellulose as a pharmaceutical auxiliary substance, pharmaceutical packs containing these tablets, the use of dichloromethylenediphosphonic acid together with microcrystalline cellulose for the production of a tablet with improved bioavailability as well as the process for producing this tablet.

It is known that the substance dichloromethylenediphosphonic acid, which is also known under the name clodronate, is used in pharmaceutical agents to treat osteolysis resulting from bone metastases of solid tumours as well as to treat hypercalcaemia (cf. e.g. DE-18 13 659). In the meantime it has also turned out that biphosphonates such as e.g. clodronic acid or their physiologically tolerated salts can be used successfully in the treatment of osteoporosis and osteoporotic pain.

In order to treat osteolysis the compound has to be administered in a relatively high dosage over a long period in order to develop its effect. The preparation Ostac® capsules contains the active substance in the form of its sodium salt (clodronic acid, disodium salt x 4 $H_2O$; MW: 360 g/mol) in an amount of 500 mg per capsule. With respect to the active substance clodronic acid (MW=244.9 g/mol) this corresponds to an amount of about 340 mg. The intake of four capsules daily and in severe cases up to eight capsules per day is necessary for the treatment. This corresponds to a daily dose to be administered of 1360–2720 mg clodronic acid.

Due to this high dosage of the active substance that is required, forms of administration were developed first of all which contain the highest possible content of active substance in order to make the individual form of administration as small as possible. Such formulations are described in EP 0 275 468 with a content of active substance of 80–95%. The preparation Ostac® has a percentage content of the active substance disodium-clodronate tetrahydrate of about 500 mg (corresponding to 91%) with a total weight of capsule filling material of about 550 mg.

It is difficult for some patients, due to their state of health, to swallow capsules of such a size between 550–570 mg filling mass several times daily over a long period of time.

On the other hand in order to improve the patient's compliance with the mode of administration it would be desirable to reduce the daily intake of four to eight capsules since experience shows that for example a single or double administration is adhered to more resolutely than a multiple administration. With regard to the required total dose of about 1400 mg and in severe cases of about 2700 mg clodronate which has to be administered daily, this would therefore require two relatively large capsules each with a total weight of at least 1100 mg. However, such capsules are disadvantageous due to their size.

The object of the invention was to provide a form of administration of the active substance clodronic acid with increased bioavailability which enables the total dose that has to be administered daily to the patient to be reduced and thus also the number of forms of administration to be taken daily or which enables smaller forms of administration such as tablets to be used with the same frequency of administration.

It was surprisingly found that when tablets to which microcrystalline cellulose has been added are used as the form of administration, the bioavailability of the active substance is higher compared to capsules when administered to humans. This enables the daily dose of clodronic acid to be administered to be reduced to lower values. In particular it was found that the tablets according to the invention enable the total daily dose of clodronic acid to be reduced to values of up to 60%. This means that for example instead of the usual amount of 1360 mg clodronic acid, a daily total dose of about 820 mg clodronic acid has a comparable therapeutic effect.

Assuming that a patient usually has to take four capsules of the preparation Ostac® with a single dose of about 340 mg clodronic acid (corresponding to a daily total dose of 1360 mg clodronic acid), the tablets according to the invention lead to a reduction of the daily total dose to about 800–1100 mg. This represents on the one hand a reduction of the content of active substance per single dosage to about 200–270 mg clodronic acid and a reduction of the total weight of the tablet to about 350–500 mg if it is intended to retain the administration of four tablets per day. This is of particular significance for those patients that have difficulty in swallowing larger tablets. The reduction of the content of active substance provides an opportunity of reducing the total weight of the tablet which results in relatively small tablets.

In order to achieve a reduction in the frequency of administration, tablets can be produced on the other hand which replace the previously conventional administration of four Ostac® capsules. Due to the excellent bioavailability attained with the formulation according to the invention it is possible, depending on the desired daily frequency of administration, to vary the content of active substance per tablet and thus to vary as desired the size of the tablet within certain limits.

If one assumes for example a daily total dose of 1360 mg clodronic acid which was previously administered by four Ostac® capsules, then on the basis of the higher bioavailability of the active substance in the tablets according to the invention that was found in human experiments which enables a reduction of the total dose of clodronic acid to about 65% (corresponding to 884 mg clodronic acid), this daily dose can be administered by two, three or four tablets according to the invention each with a content of active substance of 442 mg, 295 mg or 221 mg clodronic acid. Hence the size of the tablet can be well adapted to the respective requirements. The larger tablets are particularly advantageous when there is a risk that the patient does not consistently comply with the required multiple daily intake and prefers a single or double administration per day. The smaller tablets are advantageous in those cases where the patient has difficulty in swallowing the larger tablets and thus prefers the administration of smaller tablets several times daily. In the case of a higher or lower daily total dose than the dose of 1360 mg clodronic acid described here as an example, the content of active substance per tablet is determined in an analogous manner according to the desired requirements with regard to frequency of application and size of the tablets.

BRIEF DESCRIPTION OF THE DRAWINGS

FIG. 1 demonstrates the time course of the average serum concentration of active substance (clodronic acid) in the blood of several patients.

The following examples elucidate some preferred embodiments of the invention:

a) A conventional Ostac® capsule (340 mg clodronic acid) can be substituted by a tablet according to the invention with a content of active substance of about 220 mg. In the case that the active substance is used in the form of the tetrahydrate of the sodium salt this means that the amount of active substance is reduced in the administrative form from 500 mg to about 325 mg.

b) Two conventional Ostac® capsules (total dose 680 mg clodronic acid) can be substituted by one tablet according to the invention with a content of active substance of about 440 mg. This means that in accordance with the details in item a) the amount of active substance is reduced from 1000 mg to 650 mg of the tetrahydrate of disodium clodronate or from 800 mg to 520 mg with respect to the anhydrous form.

c) Three conventional Ostac® capsules (total dose 1020 mg clodronic acid) can be substituted by one tablet according to the invention with a content of active substance of about 660 mg or by two tablets each of 330 mg.

d) Four conventional Ostac® capsules (total dose 1360 mg clodronic acid) can be substituted by one tablet according to the invention with a content of active substance of about 880 mg or by two tablets each with about 440 mg or three tablets each with about 300 mg clodronic acid.

The above calculation of the content of active substance in the tablet according to the invention was based on results from bioequivalence studies on humans which showed that the intake of one tablet with a content of active substance of 520 mg (referring to the anhydrous form of sodium clodronate) is bioequivalent to the intake of two conventional Ostac® capsules each with a content of 400 mg active substance. Measurement of the serum concentration of clodronic acid in the blood of several patients showed substantially comparable values over a period of 16 hours.

The tablets according to the invention can be used in particular to treat osteoporosis. Since these cases often involve a long-term therapy, the advantageous reduction of the daily dose of clodronic acid and thus the minimization of possible side effects is of particular importance.

The tablet according to the invention contains the active substance dichloromethylenediphosphonic acid in an amount of 50–900 mg, preferably of 200–700 mg with reference to the content of clodronic acid. The physiologically tolerated salts of clodronic acid are preferably used and in particular the alkali salts preferably the disodium salt, that can either be used as a tetrahydrate or in an anhydrous form. Of course other physiologically tolerated salts can also be used such as e.g. the lithium, potassium, ammonium or calcium salt or their hydrates. The percentage content of the active substance (with reference to clodronic acid) is 10–65% by weight and preferably 50–60% by weight, in particular about 55% by weight in relation to the total weight of the core of the tablet. When using sodium clodronate tetrahydrate as the reference quantity, the amount of active substance is preferably 74–88% and in particular about 80% of the total weight of the tablet.

The additive according to the invention of microcrystalline cellulose amounts to 1–20% by weight in relation to the total weight of the tablet core and in particular 5–15% by weight or 8–12% by weight. The content of microcrystalline cellulose is particularly preferably about 10% by weight. The microcrystalline cellulose is preferably used as Avicel®. Instead of microcrystalline cellulose it is also possible to use other agents which act similarly such as other modified cellulose derivatives or polyethylene glycol (PEG) 4000–6000.

The tablet in addition contains one or several conventional pharmaceutical auxiliary or carrier substances such as e.g. fillers, lubricants, disintegrants, binding agents or mould-release agents. Starches (potato, wheat and corn starch), lactose, glucose, mannitol, calcium carbonate, calcium phosphate, cellulose, talcum or other products known in the technology to fulfil this purpose come into consideration as such. The proportion of pharmaceutical auxiliary and carrier substances can be varied within wide limits depending on the selected content of active substance in the tablet and is in each case 0.1–20% by weight.

The proportion of filler substances is about 3–10%, preferably 5–7% by weight in relation to the total weight of the tablet. Corn starch, talcum and/or lactose come especially into consideration as the filler substances. The proportion of talcum is preferably about 3.5–5%, the proportion of corn starch about 2–5%, in particular about 2.5% by weight.

The tablet can contain common lubricants. Silicon dioxide, talcum and/or stearic acid or their salts come into consideration as such and in particular their magnesium or calcium salts. The total content of lubricants is up to 6% by weight in relation to the total weight of the tablet. One or several lubricants in either the same or different amounts can be used in each case. The content in each case is up to 3% by weight, in particular 0.1–2% by weight. Magnesium stearate and/or talcum is preferably used in a range of 0.2–2% by weight.

Apart from the aforementioned auxiliary substances, tablet disintegrants can in addition be added to the tablet which cause a more rapid disintegration of the tablet on contact with the stomach fluid. Such disintegrants are for example sodium carboxymethyl starch, cross-linked carmellose, cross-linked polyvidone and other agents acting similarly that can be present in amounts of up to 10% by weight, preferably up to 3% by weight in relation to the total weight of the tablet. Sodium carboxymethyl starch in a range of 1–5% by weight, preferably 1–2% by weight is preferably used as a disintegrant.

The tablet core which serves as a reference quantity for the calculation of the aforementioned weight ratios, can be provided with a coating. The coating can serve on the one hand to avoid the unpleasant taste of the tablet as such. In this case flavourings are added during the production of the tablet coating. The coating can also on the other hand delay the release of the active substance. Substances are used for this which, in the form of an applied diffusion film, contribute to a retarded release of the active substance.

In bioavailability studies it was shown that for example a tablet according to the invention with a content of active substance of about 420–460 mg clodronic acid exhibits a bioavailability of the active substance which corresponds to that of two conventional capsules each with about 340 mg clodronic acid. The total weight of this tablet according to the invention, which thus contains double the usual dose, is between 750–850 mg, preferably 790–810 mg when using the tetrahydrate of sodium clodronate. When using anhydrous clodronate this results in a lower total weight of the tablet due to the lower weight of active substance required. In these cases it may be expedient during the production of the tablet to reduce the amount of pharmaceutical auxiliary and carrier substances in the same proportion to correspond to the lower weight of active substance.

It is also possible using the formulation according to the invention to produce tablets with a content of active substance of 500–530 mg and a maximum total weight (with reference to sodium clodronate tetrahydrate) of 870–970, preferably 900–950 mg. Thus tablets according to the invention can be provided with single or double doses which are smaller and thus better for oral administration than those that were produced according to the previously known formulations. In the case of a previously conventional capsule with an active substance content of clodronic acid of 340 mg (corresponding to about 500 mg disodium clodronate tetrahydrate, or 400 mg anhydrous disodium clodronate), only about 220 mg active substance are necessary with the formulation according to the invention and as a result the total weight of the tablet is usually between 395–410 mg.

The tablet according to the invention also shows good dissolution properties. Thus the dissolving rate of the 440 mg dosage according to the invention (determined according to the USP paddle method) is already at least 60% after 15 minutes and 75% after 30 minutes.

The invention also concerns pharmaceutical packs containing 30–400 tablets according to the invention to be administered in a daily dose of one to three, preferably two tablets (content of active substance 420–460 or 500–530 mg) or four to eight, preferably four tablets (content of active substance 200–270 mg).

In addition the invention concerns the use of the active substance dichloromethylenediphosphonic acid or of a physiologically tolerated salt thereof together with microcrystalline cellulose as a pharmaceutical auxiliary substance for the production of a tablet with improved bioavailability, preferably of a tablet of conventional size with double the efficacy compared to a conventional capsule.

The tablets according to the invention are manufactured in a conventional manner by bringing the tablet mass into a suitable granulated form by granulation (dry, wet or spray granulation) before pressing. Usually the desired amount of active substance for the form of administration to be produced is mixed in a dry state with ca. 4–8% by weight of the filling substances and granulated with a conventional binding agent such as corn starch or also only with water. In addition to this other processes such as compacting can also be used. The granulate obtained in this manner is then admixed with 5–15% by weight microcrystalline cellulose, up to 6% by weight lubricant and up to 3% by weight disintegrant in a commercial mixing apparatus and mixed. After the mixing process the granulate is tabletted or if desired sprayed beforehand with an aroma solution and stored for permeation. In order to improve the taste the finished tablet can also be coated with a film.

The details of dosage given in the following examples of application refer to the content of clodronic acid (MW=244.9). In order to convert this into the content of disodium clodronate, anhydrous (MW=288.9) the conversion factor is about 1.18, in the case of the tetrahydrate (MW=360.9) about 1.47.

EXAMPLE 1

Tablets with a Content of Active Substance of 440 mg Clodronic Acid a) The production of a batch size of 200,000 tablets with a content of active substance of 440 mg clodronic acid (corresponding to 520 mg sodium clodronate, anhydrous; or 650 mg sodium clodronate tetrahydrate) is described in the following.

| Pos. 1: | clodronic acid disodiumtetrahydrate | 129945.4 g |
|---|---|---|
| Pos. 2: | corn starch | 3900.0 g |

-continued

| Pos. 3: | talcum | 5980.0 g |
|---|---|---|
| Pos. 4: | sodium carboxymethyl starch | 2654.6 g |
| Pos. 5: | magnesium stearate | 520.0 g |
| Pos. 6: | microcrystalline cellulose | 15600.0 g |
| | batch weight: | 158600.0 g |

The raw materials from positions 1–3 are granulated. The additives from positions 4–6 are subsequently mixed with the granulate. The mass produced in this manner is subsequently pressed into tablets on suitable machines. The yield of optically flawless tablets is 177,215 units (88.6%).

b) When the anhydrous form of sodium clodronate is used this results, in analogy to example 1a), in the following composition of the pharmaceutical mixture:

| Pos. 1: | clodronic acid disodium salt, anhydrous | 104000.0 g |
|---|---|---|
| Pos. 2: | corn starch | 3121.3 g |
| Pos. 3: | talcum | 4786.0 g |
| Pos. 4: | sodium carboxymethyl starch | 2124.6 g |
| Pos. 5: | magnesium stearate | 416.2 g |
| Pos. 6: | microcrystalline cellulose | 12485.3 g |
| | batch weight: | 126933.4 g |

The production of the granulate and the tablet mass is carried out analogously to example 1a).

The composition of the tablet core is given in the following table:

| | dosage 440 mg |
|---|---|
| sodium clodronate × 4 H$_2$O | 649.727 |
| talcum | 29.90 |
| corn starch | 19.50 |
| microcrystalline cellulose | 78.00 |
| sodium carboxymethyl starch | 13.273 |
| magnesium stearate | 2.6 |
| weight of the tablet/mg | 793 |

The tablets are particularly suitable for an administration of 2 tablets per day and thus substitute 4 conventional Ostac capsules.

EXAMPLE 2

Tablets with a Content of Active Substance of 509 mg Clodronic Acid

The production is carried out analogously to example 1 for a batch size of 200,000 tablets with a content of active substance of clodronic acid of 509 mg (corresponding to 600 mg sodium clodronate, anhydrous; or 750 mg sodium clodronate tetrahydrate) per tablet.

| Pos. 1: | clodronic acid disodiumtetrahydrate | 150000 g |
|---|---|---|
| Pos. 2: | corn starch | 4500 g |
| Pos. 3: | talcum | 6900 g |
| Pos. 4: | sodium carboxymethyl starch | 3063 g |
| Pos. 5: | magnesium stearate | 600 g |
| Pos. 6: | microcrystalline cellulose | 18000 g |
| | batch weight: | 183063 g |

The composition per tablet core is given in the following table:

|  | dosage 509 mg |
|---|---|
| sodium clodronate × 4 H$_2$O | 749.685 mg |
| talcum | 34.50 mg |
| corn starch | 22.50 mg |
| microcrystalline cellulose | 90.00 mg |
| sodium carboxymethyl starch | 15.315 mg |
| magnesium stearate | 3.0 mg |
| weight of the tablet/mg | 915 mg |

The tablets are in particular suitable for an administration of 2 tablets per day and thus substitute 4 conventional Ostac capsules.

EXAMPLE 3

Tablet with a Content of Active Substance of 678 mg Clodronic Acid

The production is carried out analogously to example 1 for a batch size of 100,000 tablets with a content of active substance of clodronic acid of 678 mg (corresponding to 800 mg sodium clodronate, anhydrous; or 1000 mg sodium clodronate tetrahydrate) per tablet.

| Pos. 1: | clodronic acid disodiumtetrahydrate | 99958 g |
|---|---|---|
| Pos. 2: | corn starch | 3000 g |
| Pos. 3: | talcum | 4600 g |
| Pos. 4: | sodium carboxymethyl starch | 2042 g |
| Pos. 5: | magnesium stearate | 400 g |
| Pos. 6: | microcrystalline cellulose | 12000 g |
|  | batch weight: | 122000.0 g |

The composition per tablet core is given in the following table:

|  | dosage 678 mg |
|---|---|
| sodium clodronate × 4 H$_2$O | 1000.0 |
| talcum | 46.0 |
| corn starch | 30.0 |
| microcrystalline cellulose | 120.0 |
| sodium carboxymethyl starch | 20.42 |
| magnesium stearate | 4.0 |
| weight of the tablet/mg | 1220 |

The above tablet replaces ca. three conventional Ostac® capsules.

EXAMPLE 4

Tablet with a content of active substance of 220 mg clodronic acid

The production is carried out analogously to example 1 for a batch size of 300,000 tablets with a content of active substance of clodronic acid of 220 mg (corresponding to 260 mg sodium clodronate, anhydrous; or 325 mg sodium clodronate tetrahydrate) per tablet.

| Pos. 1: | clodronic acid disodiumtetrahydrate | 97459 g |
|---|---|---|
| Pos. 2: | corn starch | 4925 g |
| Pos. 3: | talcum | 4485 g |
| Pos. 4: | sodium carboxymethyl starch | 1992 g |
| Pos. 5: | magnesium stearate | 390 g |
| Pos. 6: | microcrystalline cellulose | 11700 g |
|  | batch weight: | 118951 g |

The composition per tablet core is given in the following table:

|  | dosage 220 mg |
|---|---|
| sodium clodronate × 4 H$_2$O | 324.864 |
| talcum | 14.95 |
| corn starch | 9.75 |
| microcrystalline cellulose | 39.0 |
| sodium carboxymethyl starch | 6.64 |
| magnesium stearate | 1.30 |
| weight of the tablet/mg | 396.5 |

The tablets are particularly suitable for an administration of 4 tablets per day, in severe cases of 8 tablets per day. They substitute the conventional Ostac® capsules whose total weight is 550 mg when using sodium clodronate tetrahydrate.

EXAMPLE 5

Tablet with a Content of Active Substance of 254 mg Clodtonic Acid

The production is analogous to example 1 for a batch size of 300,000 tablets with a content of active substance of clodronic acid of 254 mg (corresponding to 300 mg sodium clodronate, anhydrous; or 375 mg sodium clodronate tetrahydrate) per tablet.

| Pos. 1: | clodronic acid disodiumtetrahydrate | 112452 g |
|---|---|---|
| Pos. 2: | corn starch | 3375 g |
| Pos. 3: | talcum | 5175 g |
| Pos. 4: | sodium carboxymethyl starch | 2298 g |
| Pos. 5: | magnesium stearate | 450 g |
| Pos. 6: | microcrystalline cellulose | 13500 g |
|  | batch weight: | 137337 g |

The composition per tablet core is given in the following table:

|  | dosage 254 mg |
|---|---|
| sodium clodronate × 4 H$_2$O | 374.84 |
| talcum | 17.25 |
| corn starch | 11.25 |
| microcrystalline cellulose | 45.0 |
| sodium carboxymethyl starch | 7.66 |
| magnesium stearate | 1.50 |
| weight of the tablet/mg | 457.5 |

The tablets are particularly suitable for an administration of 4 tablets per day, in severe cases of 8 tablets per day. They substitute the conventional Ostac® capsules whose total weight is 550 mg when using sodium clodronate tetrahydrate.

EXAMPLE 6

24 patients received the usual dosage of two Ostac® capsules each with a content of active substance of 340 mg clodronic acid. The serum concentration of clodronic acid was measured according to standard methods over a period of 16 hours. The time course of the serum concentration is shown in FIG. 1 (curve +). The same group of patients received a tablet with a content of active substance of 440 mg clodronic acid. The time course of the average serum concentration of clodronic acid is largely identical compared to the group treated with Ostac® i.e. it is bioequivalent in relation to the administration of two Ostac® capsules.

We claim:

1. A tablet having a core, which is uncoated or coated, comprising an effective amount of clodronic acid or a physiologically tolerated salt thereof as the active ingredient and an amount of microcrystalline cellulose which reduces the total daily dose of clodronic acid required for human therepay therewith, by values of up to 60 percent by weight, compared to a corresponding tablet lacking microcrystalline cellulose.

2. Tablet of claim 1, wherein the microcrystalline cellulose is present in an amount which is about 5–15% by weight of the core.

3. Table of claim 1, wherein the core contains clodronic acid or salt thereof in an amount corresponding to about 200–700mg of clodronic acid.

4. Tablet of claim 1, wherein the active ingredient is in the form of the disodium salt of clodronic acid.

5. Tablet of claim 4, wherein the active ingredient is in the form of the tetrahydrate.

6. Tablet of claim 5, additionally containing a filler.

7. Tablet of claim 6, wherein the filler is corn starch or talcum.

8. Tablet of claim 1, additionally containing a lubricant and a disintegrant.

9. Tablet of claim 8, wherein the lubricant is a physiologically tolerated salt of stearic acid and the disintegrant is sodium carboxymethyl starch.

10. Tablet of claim 9, wherein the lubricant is magnesium stearate.

11. Tablet of claim 1, wherein the core has a total weight of 750–850 mg., and an active ingredient content of clodronic acid of 420–460 mg.

12. Tablet of claim 11, wherein the core has a total weight of 790–810 mg.

13. Tablet of claim 1, wherein the core has a total weight of 870–970 mg, and an active ingredient content of clodronic acid of 500–530 mg.

14. Tablet of claim 13, wherein the core has a total weight of 900–950 mg.

15. Tablet of claim 1, wherein the core has a total weight of 350–500 mg., and an active ingredient content of clodronic acid of about 200–270 mg.

16. Tablet of claim 1, wherein the core contains 10–65% by weight of active ingredient (calculated as clodronic acid) and 1–20% by weight of microcrystalline cellulose.

17. Tablet of claim 16, wherein the core contains 50–60% by weight of active ingredient (calculated as clodronic acid) and 5–15% by weight of microcrystalline cellulose.

18. Tablet of claim 17, wherein the core contains 8–12% by weight of microcrystalline cellulose.

19. Pharmaceutical pack containing about 30–400 of the tablets of claim 11 and instructions for administration in a daily dose of one to three tablets.

20. Pharmaceutical pack of claim 19, wherein the daily dose is two tablets.

21. Pharmaceutical pack containing about 30–400 of the tablets of claim 13 and instructions for administration in a daily dose of one to three tablets.

22. Pharmaceutical pack of claim 13, wherein the daily dose is two tablets.

23. Pharmaceutical pack containing about 30–400 of the tablets of claim 15 and instructions for administration in a daily dose of four to eight tablets.

24. Pharmaceutical pack of claim 23, wherein the daily dose is four tablets.

25. A method of decreasing the total daily dose of clodronic acid or a physiologically tolerated salt thereof required for human thereapy, in a tablet containing clodronic acid or physiologically tolerated salt thereof as the active ingredient, the method comprising including microcrystalline cellulose in the tablet in an amount which reduces the total daily dose of clodronic acid required for human thereapy therewith, by values of up to 60 percent by weight, compared to a corresponding tablet lacking microcrystalline cellulose.

26. A method of reducing the drug load on a patient receiving osteoporosis treatment comprising the administration of clodronic acid or physiologically tolerated salt thereof, said method comprising administering the clodronic acid or salt thereof in a tablet which contains microcrystalline cellulose in an amount which reduces the total daily dose of clodronic acid required for human therapy therewith, by values of up to 60 percent by weight, compared to a corresponding tablet lacking microcrystalline cellulose.

27. A process for the production of a tablet containing clodronic acid or a physiologically tolerated salt thereof, the method comprising mixing the clodronic acid or salt thereof with microcrystalline cellulose in an amount which reduces the total daily dose of clodronic acid required for human therapy therewith, by values of up to 60 percent by weight, compared to a corresponding tablet lacking microcrystalline cellulose, and pressing the mixture into tablets.

28. Method of claim 27, wherein the process includes the steps of mixing the clodronic acid or salt thereof with about 4–8% by weight of at least one filler to form a first mixture, granulating the first mixture with a binding agent, mixing the granulated first mixture with about 5–15% by weight of microcrystalline cellulose, up to 3% by weight of disintegrant and up to 6% by weight of lubricant to form a second mixture, and tabletting the second mixture.

29. Method of claim 28, including the further step of coating the tabletted product to improve taste or to retard release of the clodronic acid or a physiologically tolerated salt thereof.

30. Process of claim 28, wherein the first mixture contains 6–7% by weight of filler, and the granulated first mixture is mixed with 8–12% by weight of microcrystalline cellulose, up to 2% by weight of disintegrant and up to 3% by weight of lubricant.

31. Process of claim 28, wherein the filler is corn starch and/or talcum.

32. Process of claim 28, wherein the lubricant is magnesium stearate and the disintegrant is sodium carboxymethyl starch.

* * * * *